US010856947B2

(12) United States Patent
Hongo et al.

(10) Patent No.: US 10,856,947 B2
(45) Date of Patent: Dec. 8, 2020

(54) GRIP FORCE SENSATION FEEDBACK DEVICE AND STYLUS-TYPE FORCE SENSATION FEEDBACK DEVICE

(71) Applicant: SONY CORPORATION, Tokyo (JP)

(72) Inventors: Kazuo Hongo, Kanagawa (JP); Hiroyuki Suzuki, Tokyo (JP); Yasunori Kawanami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 201 days.

(21) Appl. No.: 16/063,600

(22) PCT Filed: Dec. 1, 2016

(86) PCT No.: PCT/JP2016/085732
§ 371 (c)(1),
(2) Date: Jun. 18, 2018

(87) PCT Pub. No.: WO2017/130562
PCT Pub. Date: Aug. 3, 2017

(65) Prior Publication Data
US 2018/0368931 A1 Dec. 27, 2018

(30) Foreign Application Priority Data

Jan. 26, 2016 (JP) .................................. 2016-012194

(51) Int. Cl.
*A61B 34/00* (2016.01)
*A61B 34/37* (2016.01)
(Continued)

(52) U.S. Cl.
CPC .............. *A61B 34/76* (2016.02); *A61B 34/37* (2016.02); *A61B 34/74* (2016.02); *B25J 13/025* (2013.01);
(Continued)

(58) Field of Classification Search
CPC .......... A61B 34/76; B25J 13/025; G06F 3/016
See application file for complete search history.

(56) References Cited

U.S. PATENT DOCUMENTS

2003/0135203 A1* 7/2003 Wang ..................... A61B 34/37
606/1
2008/0046122 A1* 2/2008 Manzo ................... A61B 34/74
700/245
(Continued)

FOREIGN PATENT DOCUMENTS

JP 2007-510232 A 4/2007
JP 2008-123061 A 5/2008
(Continued)

OTHER PUBLICATIONS

International Search Report dated Feb. 28, 2017 in PCT/JP2016/085732, 1 page.

*Primary Examiner* — Eric D. Bertram
(74) *Attorney, Agent, or Firm* — Xsensus LLP

(57) ABSTRACT

A grip force sensation feedback device including a first rotary member that has an outer peripheral surface including a part of a first virtual conical surface, the first rotary member being rotated around a first cone axis; a second rotary member that has an opposed surface which includes a part of a second virtual conical surface and which is opposed to the outer peripheral surface of the first rotary member, the second rotary member being rotated around a second cone axis; a wire that has both end portions connected to the second rotary member and that has a central portion wound around the first rotary member; and a driving portion that provides a force sensation feedback to a finger of a user in contact with the second rotary member by rotating the first rotary member and thereby causing a rotation of the second rotary member.

17 Claims, 14 Drawing Sheets

(51) Int. Cl.
  *G06F 3/01* (2006.01)
  *B25J 13/02* (2006.01)
  *B25J 3/00* (2006.01)

(52) U.S. Cl.
  CPC ............... *G06F 3/01* (2013.01); *G06F 3/016* (2013.01); *A61B 2034/715* (2016.02); *B25J 3/00* (2013.01); *B25J 13/02* (2013.01)

(56) References Cited

U.S. PATENT DOCUMENTS

| | | | | |
|---|---|---|---|---|
| 2008/0059131 | A1* | 3/2008 | Tokita | G06F 3/0346 703/5 |
| 2011/0288573 | A1* | 11/2011 | Yates | A61B 17/07207 606/170 |
| 2014/0214206 | A1* | 7/2014 | Steinberg | G06F 3/016 700/258 |
| 2014/0276938 | A1* | 9/2014 | Hsu | A61B 34/30 606/130 |
| 2017/0121129 | A1* | 5/2017 | Mylonas | B25J 9/1689 |
| 2017/0290601 | A1* | 10/2017 | Hongo | B25J 3/00 |

FOREIGN PATENT DOCUMENTS

| | | |
|---|---|---|
| JP | 2011-48651 A | 3/2011 |
| WO | WO 2011/049013 A1 | 4/2011 |

* cited by examiner

GRIP FORCE SENSATION FEEDBACK DEVICE AND STYLUS-TYPE FORCE SENSATION FEEDBACK DEVICE

TECHNICAL FIELD

The present disclosure relates to a grip force sensation feedback device and a stylus-type force sensation feedback device.

BACKGROUND ART

For example, when performing endoscopic surgery, a medical apparatus that allows an operator to reach an affected area without largely incising a patient body, is used. In such a medical apparatus, an operator (a user) such as a surgeon remotely operates an operation apparatus including an input interface. Then, a robot apparatus provided with a surgical instrument is operated in accordance with the operation of the operator to perform surgery. In such a medical apparatus, the input interface is an essential structure as a device to be directly operated by the user.

In the medical apparatus, a surgical instrument used in the endoscopic surgery includes a surgical instrument that holds an affected area with a plurality of constituting portions (hereinafter also referred to as a "grip-type surgical instrument") as represented by forceps, tweezers, a cutting implement, or the like. In order to reduce a size or weight of the input interface for remotely operating the grip-type surgical instrument, a grip interface using a cam structure is used. However, in the grip interface using the cam structure, a reduction ratio is gradually changed depending on an angle, such as a cam angle, formed by a constituting portion and there is difficulty in improving smoothness and durability due to friction between cams. Further, there is a grip interface configured to transmit power along a parallel axis using a wire. However such a grip interface tends to become large due to an enlarged mechanism portion.

As a countermeasure against the above, Patent literature 1 discloses a power transmission mechanism that transmits the power along a nonparallel axis using a belt. Specifically, Patent literature 1 proposes a nonparallel axis transmission mechanism that uses a plurality of conical pulleys and a fan belt having a fan shape in a developed plan view as a power transmission medium that transmits the power inputted in any of the plurality of the conical pulleys to another pulley having a nonparallel rotation axis therewith. Further, Patent literature 2 discloses, as an interface usable for surgery, a force reflecting haptic interface that includes three degrees of freedom and a user interface. Specifically, Patent literature 2 proposes the force reflecting haptic interface having a user connection portion constituted by a stylus-type apparatus to be gripped by a user.

CITATION LIST

Patent Literature

Patent Literature 1: WO 2011-049013
Patent Literature 2: JP 2007-510232T

DISCLOSURE OF INVENTION

Technical Problem

However, the power transmission mechanism using a belt as a power transmission medium may cause a large noise when transmitting a feeble force because the belt itself is hard. Further, using the belt as the power transmission medium requires a larger conical pulley to increase a reduction ratio, which may increase a size of the apparatus. Thus, there is a demand for a compact grip interface capable of offering light and smooth operation feeling as a grip interface that is operated by the user and provides a force sensation feedback to a gripping force.

Solution to Problem

According to the present disclosure, there is provided a grip force sensation feedback device including: a first rotary member that has an outer peripheral surface including a part of a first virtual conical surface, the first rotary member being rotated around a first cone axis; a second rotary member that has an opposed surface which includes a part of a second virtual conical surface and which is opposed to the outer peripheral surface of the first rotary member, the second rotary member being rotated around a second cone axis; a wire that has both end portions connected to the second rotary member and that has a central portion wound around the first rotary member; and a driving portion that provides a force sensation feedback to a finger of a user in contact with the second rotary member by rotating the first rotary member and thereby causing a rotation of the second rotary member.

In addition, according to the present disclosure, there is provided a stylus-type force sensation feedback device including: a rotary member that rotates with a gripping operation performed by a user; and a driving portion that provides a force sensation feedback to the user by applying a rotation torque to the rotary member in a direction opposite to a rotation direction caused by the gripping operation performed by the user.

Advantageous Effects of Invention

As described above, according to the present disclosure, the user operable grip force sensation feedback device can be made compact while offering light and smooth operation feeling.

Note that the of described above are not necessarily limitative. With or in the place of the above effects, there may be achieved any one of the effects described in this specification or other effects that may be grasped from this specification.

MODE(S) FOR CARRYING OUT THE INVENTION

Figure 1:
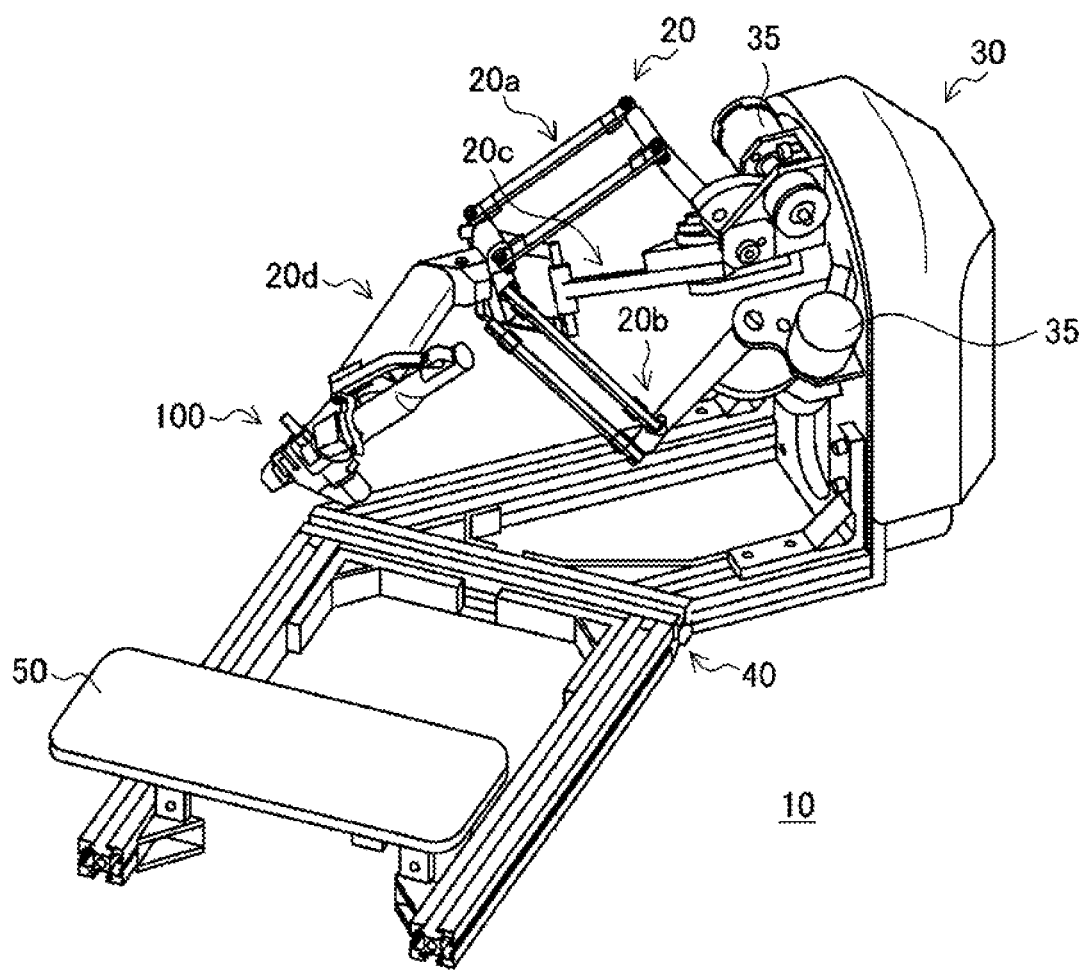
FIG. 1 is an illustration showing a perspective view of a medical apparatus according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be provided in the following order.
1. Overall configuration of medical apparatus
2. Overall configuration of grip force sensation feedback device (stylus-type force sensation feedback device)
3. Power transmission mechanism
4. Usage example
    4-1. Remote operation of grip-type surgical instrument
    4-2. Force sensation feedback
    4-3. Origin returning operation
5. Summary <1. Overall Configuration of Medical Apparatus>

First, a schematic configuration of a medical apparatus 10 including a grip force sensation feedback device 100 according to an embodiment of the present disclosure will be described by referring to FIG. 1. FIG. 1 shows a perspective view of the medical apparatus 10 according to the present embodiment. The medical apparatus 10 shown in FIG. 1 constitutes a master-slave type medical robot apparatus together with a slave side robot apparatus not illustrated. Such a medical apparatus 10 can be configured as a master side operation input apparatus that remotely operates the slave side robot apparatus by sending an operation command to the slave side robot apparatus using a wired or wireless communication means. The slave side robot apparatus operated by the medical apparatus 10 may be a robot apparatus that is provided with an arm of, for example, 6 degrees of freedom having a grip-type surgical instrument, such as forceps, tweezers, a cutting implement, or the like, at its tip end. The slave side robot apparatus changes a position and direction of the grip-type surgical instrument and performs a gripping operation of the grip-type surgical instrument on the basis of the operation command from the medical apparatus 10.

The medical apparatus 10 includes a supporting arm portion 20, a main body portion 30, a base portion 40, and the grip force sensation feedback device 100. The base portion 40 is a base portion of the medical apparatus 10 and may be configured, for example, by combining a frame material made of aluminum. However, the configuration of the base portion 40 is not limited to such an example. The base portion 40 is provided with a supporting stand 50 on which a user such as a surgeon can place his/her elbow. The user operates the grip force sensation feedback device 100 while placing his/her elbow or arm on the supporting stand 50 to maintain a stable operation. Note that the supporting stand 50 may not be attached to the base portion 40 or may not be included as a constituent element of the medical apparatus 10.

The supporting arm portion 20 is supported by the main body portion 30 on a rear end side and supports the grip force sensation feedback device 100 on a front end side. The supporting arm portion 20 includes a first arm portion 20a, a second arm portion 20b, a third arm portion 20c, and a fourth arm portion 20d. The first arm portion 20a, the second arm portion 20b, and the third arm portion 20c are connected to the fourth arm portion 20d on their front end sides and connected to the main body portion 30 on their rear end sides. The first arm portion 20a, the second arm portion 20b, and the third arm portion 20c are each configured such that a plurality (two in an illustrated example) of links are rotatably connected to each other. Further, the first arm portion 20a, the second arm portion 20b, and the third arm portion 20c, and the fourth arm portion 20d are also rotatably connected to each other at their connection portions. Further, the first arm portion 20a, the second arm portion 20b, and the third arm portion 20c, and the main body portion 30 are also rotatably connected to each other at their connection portions.

The connection portions of the plurality of the links serve as joint portions, and angles of the links can be freely changed at the joint portions. Having such a configuration can freely change a position in a space of the grip force sensation feedback device 100 supported on the front end side of the supporting arm portion 20. Further, the fourth arm portion 20d supports the grip force sensation feedback device 100 on a front end side and is connected to the first arm portion 20a, the second arm portion 20b, and the third arm portion 20c on a rear end side. The fourth arm portion 20d is constituted by connecting a plurality (two in an illustrated example) of arms and these arms are axially rotatably connected to each other. Having such a configuration can freely change a direction of the grip force sensation feedback device 100 supported on the front end side of the supporting arm portion 20.

The joint portions, that is, the connection portions of the first arm portion 20a, the second arm portion 20b, and the third arm portion 20c of the supporting arm portion 20, are each provided with a sensor that detects a rotation angle of the corresponding link. Further, the fourth arm portion 20d is provided with sensors each of which detects an axial rotation angle of the corresponding arm. As the sensors for detecting these rotation angles, for example, an encoder may be used. A sensor signal of each sensor is sent to a control portion, not illustrated, provided in the main body portion 30.

Further, the main body portion 30 include motors 35 (one of them is not illustrated) that control the rotation of the links at the connection portions between the first arm portion 20a, the second arm portion 20b, and the third arm portion 20c, and the main body portion 30. Three motors 35 apply a reaction force to a movement of the grip force sensation feedback device 100 operated by the user to provide a force sensation feedback to the moving operation of the grip force sensation feedback device 100.

The grip force sensation feedback device 100 functions as a grip interface for operating a surgical instrument supported by the slave side robot apparatus not illustrated. Changing the position and direction of the grip force sensation feedback device 100 by the user causes a change in an attitude of the supporting arm portion 20, thereby changing the rotation angles of the joint portions and the axial rotation angles of the arms. The control portion controls an attitude of an arm of the slave side robot apparatus supporting the surgical instrument on the basis of information regarding the rotation angles detected by the sensors, thereby making it possible to change a position and direction of the surgical instrument supported by the slave side robot apparatus. In this operation, the control portion may provide a force sensation feedback to the moving operation of the grip force sensation feedback device 100 by detecting an external force applied to the arm of the slave side robot apparatus and controlling driving forces of three motors 35 on the basis of the external force.

Further, when the user performs a gripping operation using the grip force sensation feedback device 100, the control portion allows the grip-type surgical instrument supported by the slave side robot apparatus to perform a gripping operation on the basis of a specific operation signal obtained from the grip force sensation feedback device 100. In this operation, the control portion may provide a force sensation feedback to the gripping operation of the grip force sensation feedback device 100 by detecting an external force applied to the grip-type surgical instrument supported by the slave side robot apparatus and controlling a driving force of a motor 187 provided in the grip force sensation feedback device 100 on the basis of the external force.

Note that the supporting arm portion 20 including the sensors for detecting the rotation angles of the joint portions and the axial rotation angles of the arms may be constituted from a conventionally known supporting arm device and thus detailed description of a configuration of the supporting arm portion 20 is omitted. Further, a specific method of controlling an attitude of the arm of the slave side robot apparatus on the basis of the attitude of the supporting arm portion 20 can be also achieved by employing a conventionally known control technology and thus detailed description of the control portion is omitted.

2. Overall Configuration of Grip Force Sensation Feedback Device>

Figure 2:
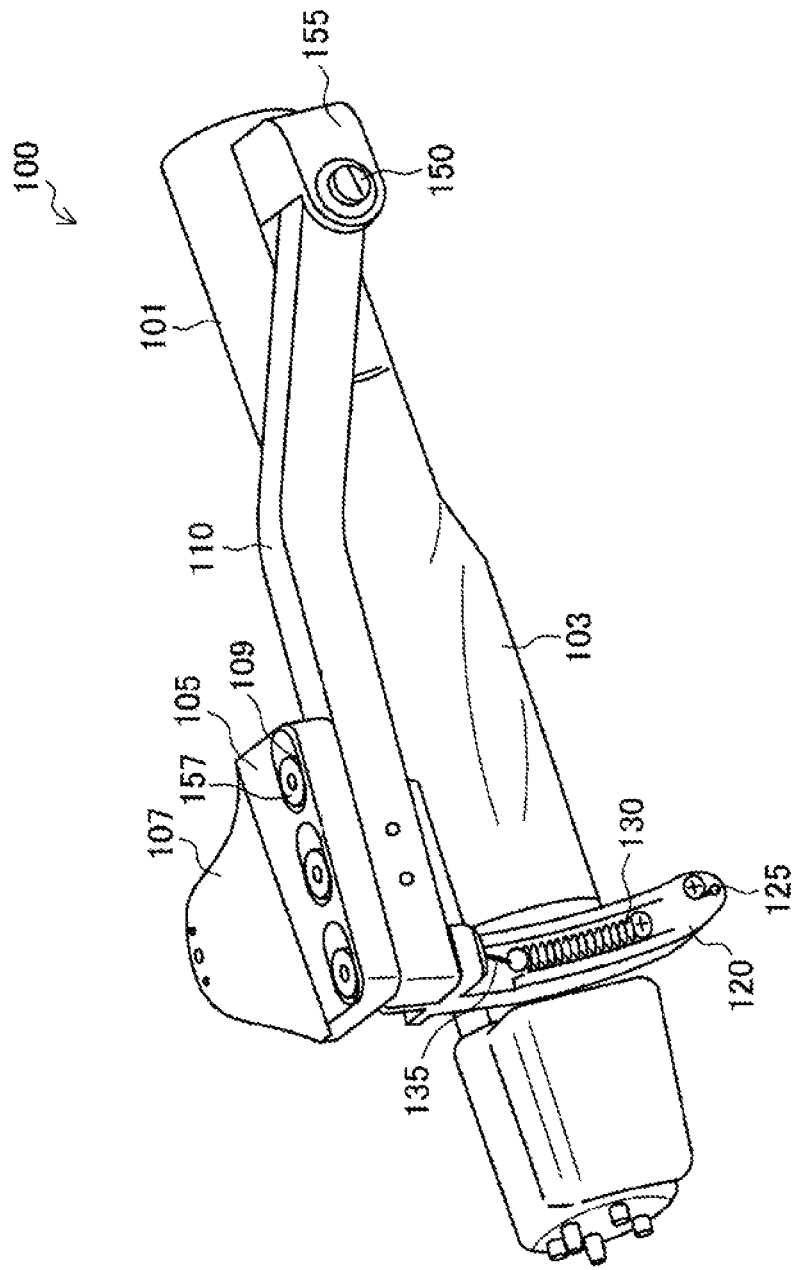
FIG. 2 is an illustration showing a perspective view of a grip force sensation feedback device according to the embodiment.
Figure 3:
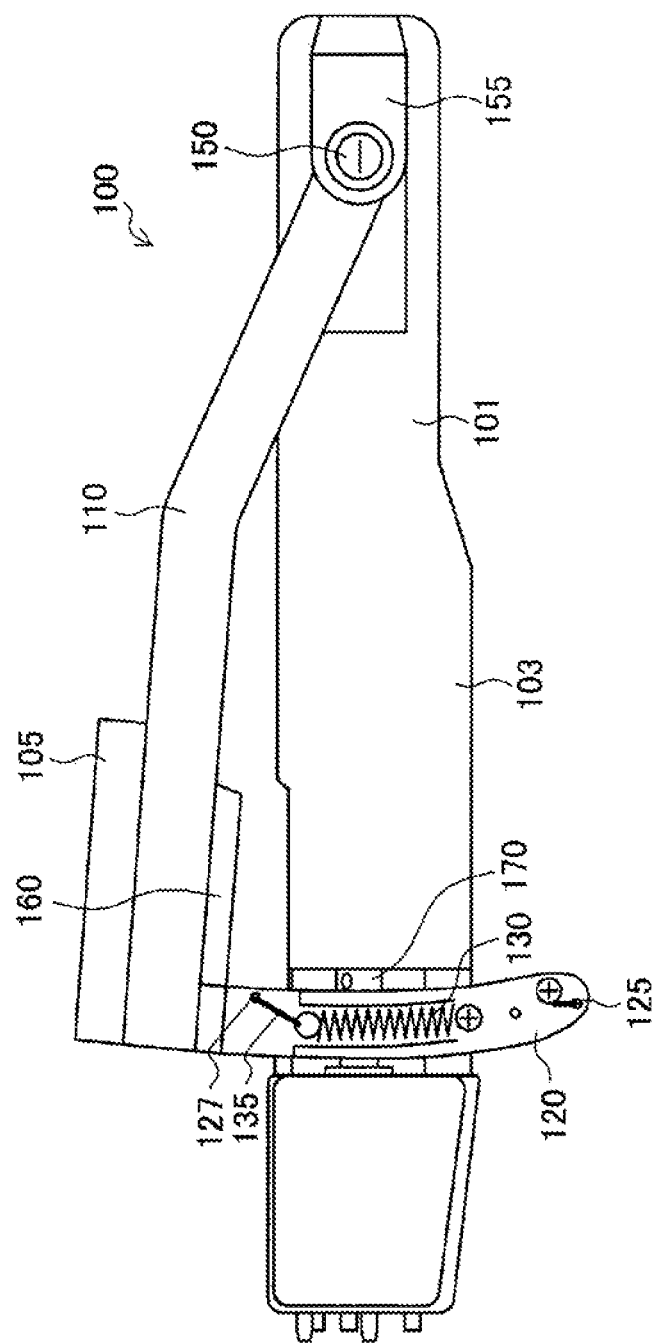
FIG. 3 is an illustration showing a side view of the grip force sensation feedback device according to the embodiment.
Figure 4:
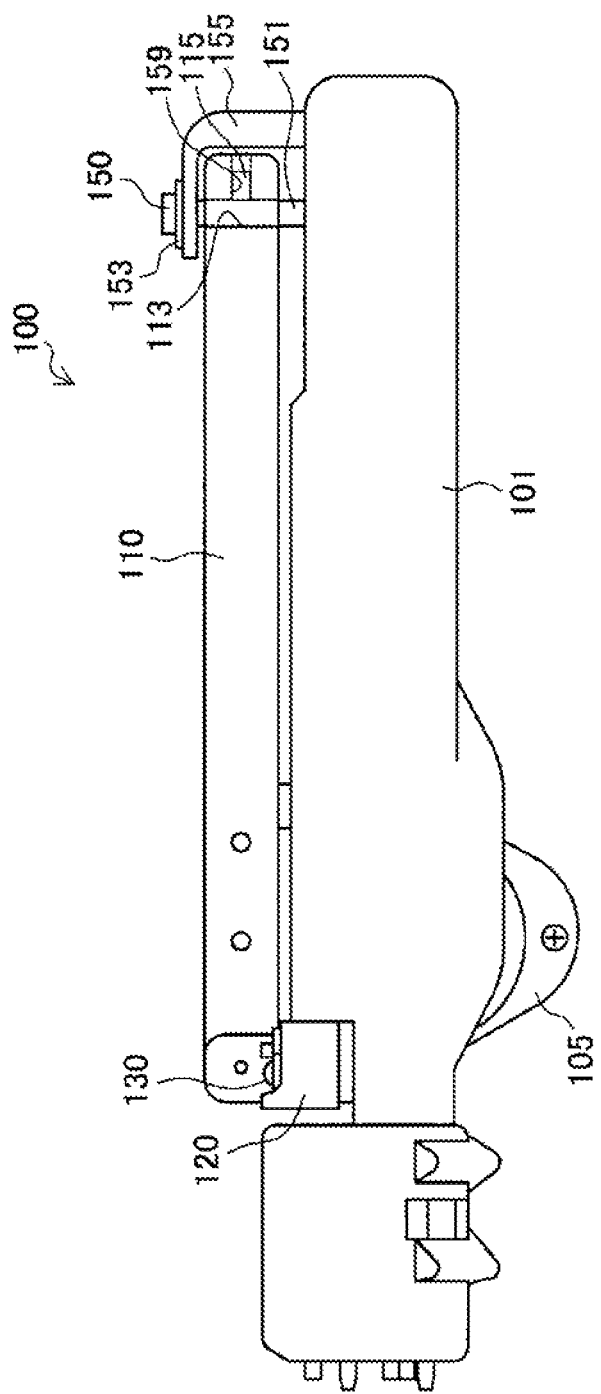
FIG. 4 is an illustration showing a bottom view of the grip force sensation feedback device according to the embodiment.
Figure 5:
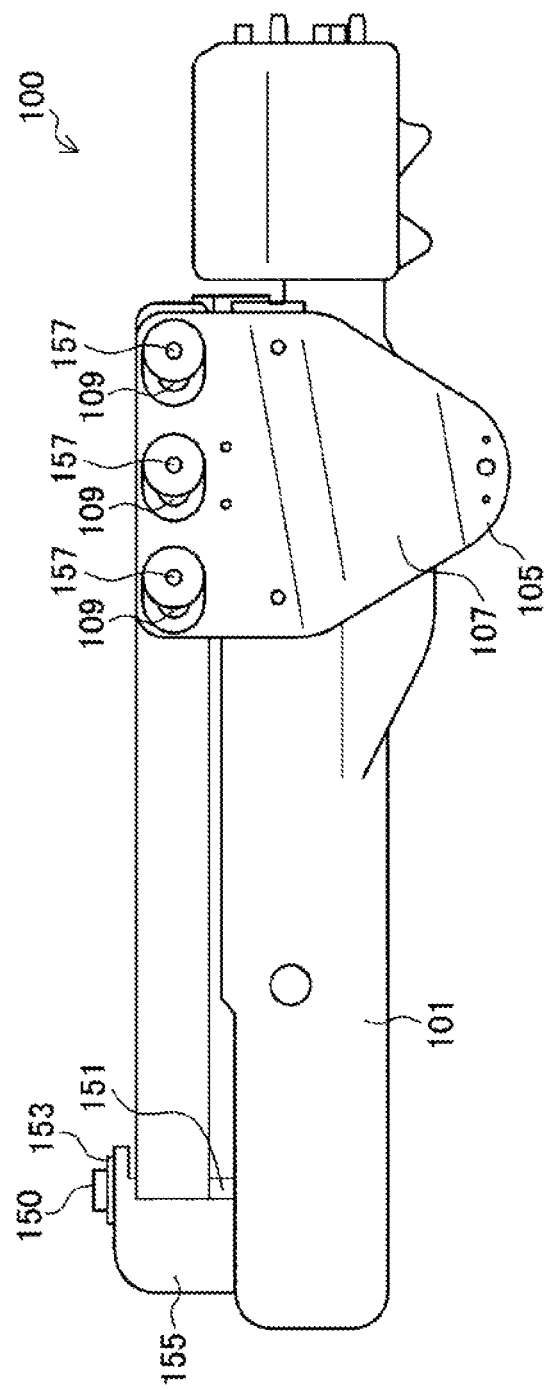
FIG. 5 is an illustration showing a top view of the grip force sensation feedback device according to the embodiment.
Figure 6:
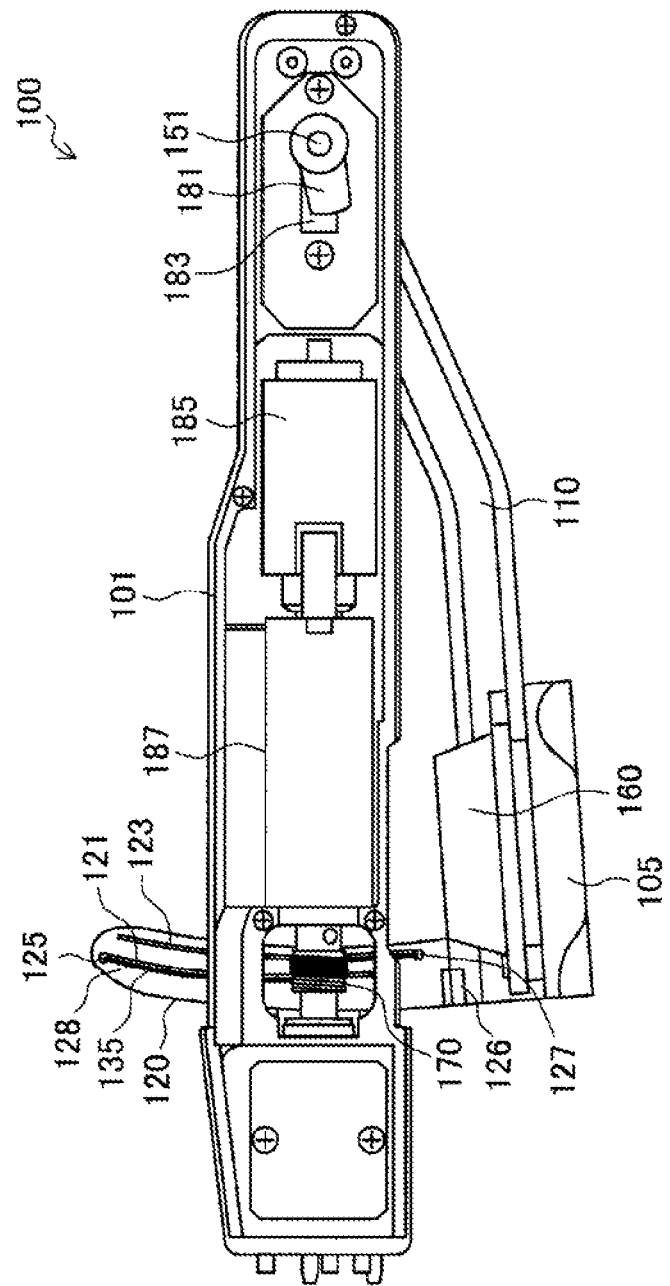
FIG. 6 is an explanatory illustration of an internal structure of the rip force sensation feedback device according to the embodiment.

Next, a configuration of the grip force sensation feedback device 100 according to the present embodiment will be described by referring to FIG. 2 to FIG. 6. FIG. 2 shows a perspective view of the grip force sensation feedback device 100, FIG. 3 shows a side view of the grip force sensation feedback device 100 in FIG. 2 viewed from a proximal side, FIG. 4 shoes a bottom view of the grip force sensation feedback device 100 in FIG. 2 viewed from a lower side, and FIG. 5 shows a top view of the grip force sensation feedback device 100 in FIG. 2 viewed from an upper side. Further, FIG. 6 is an explanatory illustration of an internal structure of the grip force sensation feedback device 100 and shows an internal transparent view of the grip force sensation feedback device 100 in FIG. 2 viewed from a distal side.

The grip force sensation feedback device 100 includes a casing 101 that contains in its inside a motor 187 and an encoder 185. A constituent material of the casing 101 is not particularly limited. The casing 101 may be formed of, for example, a resin material, aluminum, or the like for reducing the weight of the grip force sensation feedback device 100. The casing 101 is formed in a long bar shape as an overall external appearance to facilitate a gripping performance of the user. That is, the grip force sensation feedback device 100 according to the present embodiment is formed as so-called a stylus-type force sensation feedback device.

The encoder 185 corresponds to a position detecting sensor for detecting a rotation angle of the motor 187. A means for detecting the rotation angle of the motor 187 is not limited to the encoder 185. An output shaft of the motor 187 is arranged alone a longitudinal direction of the grip force sensation feedback device 100 and connected to a pulley 170 arranged on a front side of the grip force sensation feedback device 100. In this configuration, the pulley 170 is made rotatable around an axis by a driving torque of the motor 187. The pulley 170 corresponds to a first rotary member according to the present disclosed technology and the motor 187 corresponds to a driving portion according to the present disclosed technology. The pulley 170 is exposed to an outside of the casing 101 and an outer peripheral surface 171 of the pulley 170 is opposed to a rail portion 120 on one side of grip force sensation feedback device 100. The outer peripheral surface 171 of the pulley 170 is formed by a part of a virtual conical surface (a first virtual conical surface) having a cone axis (a first cone axis) coincided with an axis of the output shaft of the motor 187.

A rotating shaft member 151 is provided on a rear end side of the casing 101. A link 110 is connected to the rotating shaft member 151 rotatably around the rotating shaft member 151. Both ends of the rotating shaft member 151 are supported by a bearing portion 155 and the casing 101. The link 110 is a long member arranged on one side of the grip force sensation feedback device 100 along a longitudinal direction thereof. The link 110 is extended along a direction intersecting with the axial direction of the rotating shaft member 151. A finger contact portion 105 having a surface that intersects with a rotation direction of the link 110 and extends along the longitudinal direction of the grip force sensation feedback device 100 is provided at an appropriate position on a tip side of the link 110. The finger contact portion 105 includes a mounting portion 107 on which, for example, the user's forefinger is placed. The mounting portion 107 is recessed inward in an arch shape so as to fit to a shape of the user's finger.

A thumb contact portion 103 on which the user's thumb is placed is arranged on a part of a side surface of the casing 101 in a side where the link 110 is provided. Further, a middle finger contact portion on which the user's middle finger is placed is arranged on a part of a side surface of the casing 101 in a side opposite to the side where the link 110 is provided. In FIG. 6, a part of the casing 101 is shown as transparent and the middle linger contact portion is not illustrated. In the grip force sensation feedback device 100 according to the present embodiment, the user's right hand thumb is placed on the thumb contact portion 103 of the casing 101, the middle finger is placed on the middle finger contact portion of the casing 101, and further the forefinger is placed on the mounting portion 107 of the finger contact portion 105, so that the user can grip the grip force sensation feedback device 100 like a writing pen. That is, the grip force sensation feedback device 100 is formed in a shape that the user is accustomed to grip.

Note that, in the grip force sensation feedback device 100 according to the present embodiment, the finger contact portion 105 is fixed to the link 110 with 3 fixing screws 157. Screw holes 109 in which the fixing screws 157 are inserted are formed as long holes having their longitudinal directions along a front-back direction of the link 110. Thus, a position of the finger contact portion 105 can be adjusted in the longitudinal direction in accordance with a length of the user's finger.

Further, in the casing 101, the rotating shaft member 151 is provided with an origin sensor for setting an origin position (a reference position) of the link 110. In the grip force sensation feedback device 100 according to the present embodiment, the origin sensor includes an origin position setting implement 181 that is connected to the link 110 and rotated with the link 110 and an origin sensor base board 183 for detecting a position (a rotation angle) of the origin position setting implement 181. These origin position setting implement 181 and origin sensor base board 183 may be housed inside the casing 101. Such an origin sensor may set the origin (a reference angle) by determining the presence/absence of an edge of the origin position setting implement 181 that rotates with the rotation of the link 110, that is, by determining a detection boundary of the origin position setting implement 181 by the origin sensor base board 183.

Further, a screw hole 115 connected to a hole portion 113 in which the rotating shaft member 151 is inserted is provided on a rear end surface of the link 110. A fixing screw 159 is arranged inside the screw hole 115 (see FIG. 4). A tip of the fixing screw 159 is abutted to the rotating shaft member 151, so that the link 110 is fixed by being pressed by the rotating shaft member 151. Thus, the position of the link 110 can be adjusted along an axial direction of the rotating shaft member 151 by loosening the fixing screw 159, moving the link 110 to an appropriate position, and then tightening the fixing screw 159 again. In this manner, positions of the finger contact portion 105 and the rail portion 120 attached to the link 110 can be adjusted. In the present embodiment, such a fixing screw 159 corresponds to an adjusting portion according to the present disclosure for adjusting a distance between the outer peripheral surface 171 of the pulley 170 and an opposed surface 128 of the rail portion 120.

The rail portion 120 that extends toward the rotation direction of the link 110 is provided on the tip side of the link 110. The rail portion 120 corresponds to a second rotary member according to the present disclosed technology. The rail portion 120 having a substantially arcuate outer shape rotates along an extending direction of the rail portion 120 with the rotation of the link 110. That is, the rail portion 120 rotates around the rotating shaft member 151. The rail portion 120 includes the opposed surface 128 that is opposed to the outer peripheral surface 171 of the pulley 170. The opposed surface 128 is formed by a part of a virtual conical surface (a second virtual conical surface) having the rotating shaft member 151 as a cone axis (a second cone axis).

A wire 135 is wound around a wire groove 173 of the pulley 170. Both end portions of such a wire 135 are arranged on the rail portion 120 and a central portion of the wire 135 is wound around the pulley 170. The wire 135 functions as a member that transmits a power and a driving torque generated by the motor 187 is transmitted to the rail portion 120 via the pulley 170 and the wire 135. On the other hand, in a case where the rail portion 120 is rotated, a rotation torque of the rail portion 120 can be transmitted to the motor 187 via the wire 135 and the pulley 170. A diameter of the wire 135 may be set to, for example, 0.2 to 0.5 mm. Details of the power transmission mechanism will be described below.

Further, a force sensor may be provided between the grip force sensation feedback device 100 and the fourth arm portion 20*d* of the supporting arm portion 20. For example, the force sensor may be configured as a six-axis force sensor that detects 6 axis components in 3 directions of a force and torsion applied to the grip force sensation feedback device 100. In a case where a translational force or a force in a torsional direction is applied to the grip force sensation feedback device 100, the force sensor generates an output corresponding to a moment of such a force. The control portion detects the moment and controls an operation of the arm of the slave side robot apparatus on the basis of the moment. This allows a smooth movement of the grip-type surgical instrument supported by the slave side robot apparatus.

In such a grip force sensation feedback device 100, the origin sensor base board 183, the motor 187, the encoder 185, and the force sensor are electrically connected to the control portion of the main body portion 30 via corresponding cables not illustrated. In this configuration, detection signals of the origin sensor base board 183, the encoder 185, and the force sensor are outputted to the control portion and a control signal is inputted from the control portion to the motor 187. Note that, in the medical apparatus 10 according to the present embodiment, the control portion that controls the grip force sensation feedback device 100 is arranged in the main body portion 30, however, the control portion may be installed in the casing 101.

<3. Power Transmission Mechanism>

Hitherto the overall configuration of the grip force sensation feedback device 100 has been described. Next, a configuration of the power transmission mechanism in the grip force sensation feedback device 100 will be described in detail. As described above, in the grip force sensation feedback device 100, the driving torque of the motor 187 can be transmitted to the rail portion 120 via the pulley 70 and the wire 135. Further, in the grip force sensation feedback device 100, the rotation torque generated when the rail portion 120 is rotated by the user can also be transmitted to the motor 187 via the wire 135 and the pulley 170.

Figure 7:
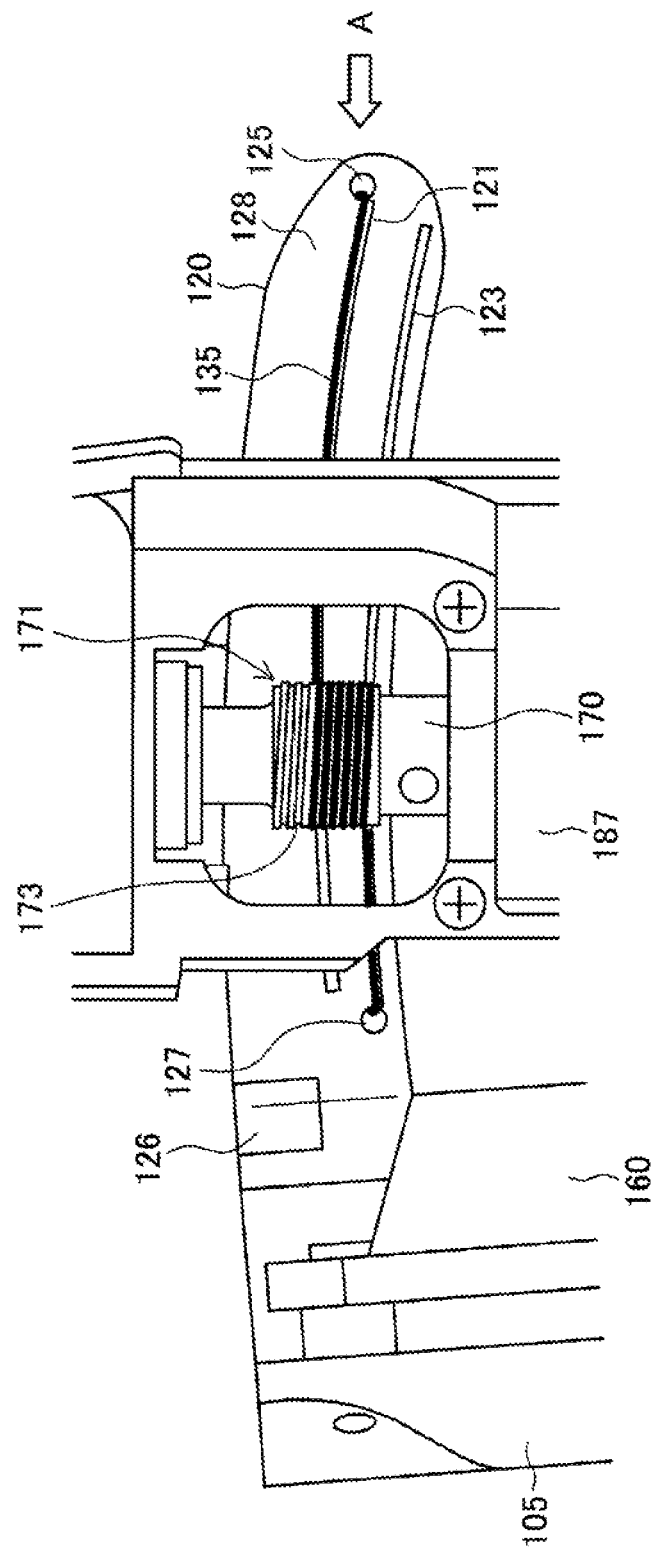
FIG. 7 is an enlarged explanatory illustration of a power transmission portion.
Figure 8:
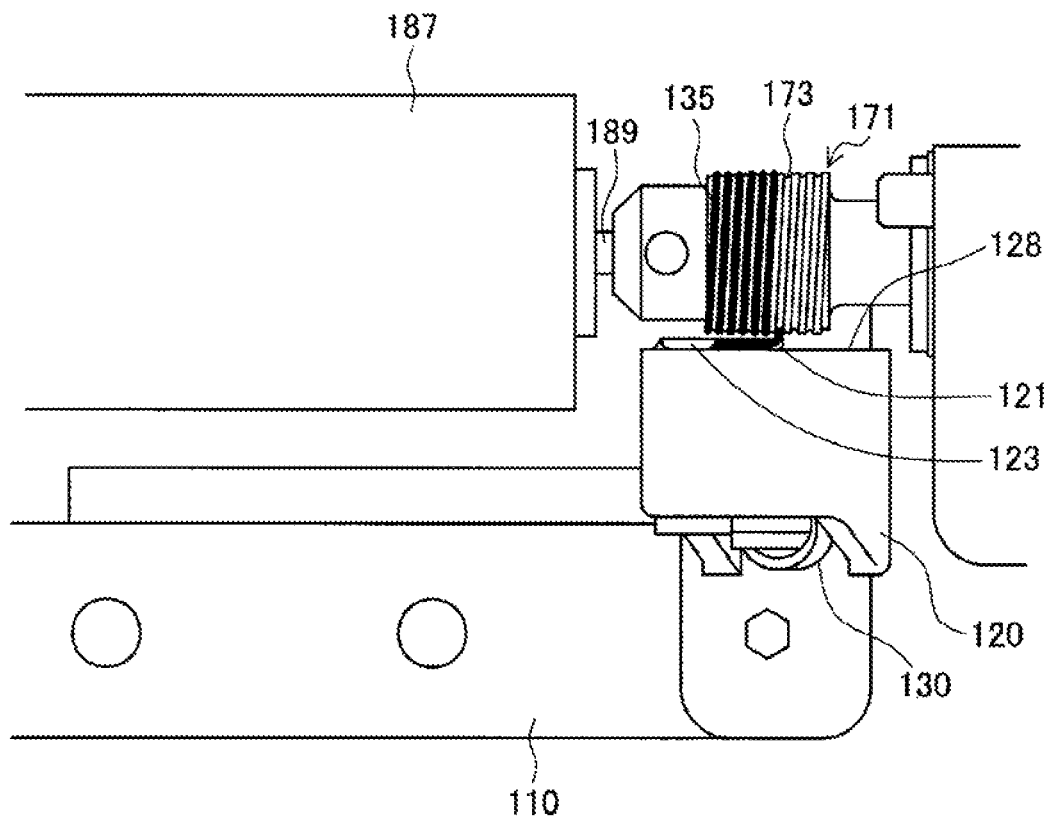
FIG. 8 is an illustration of the power transmission portion in FIG. 7 viewed from a direction of arrow A.
Figure 9:
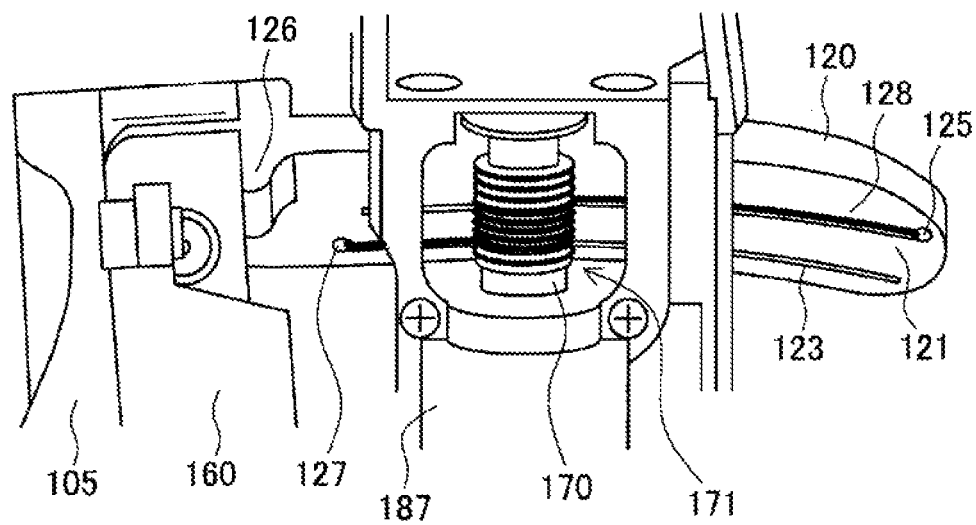
FIG. 9 is an illustration showing a perspective view of the power transmission portion.

FIG. 7 to FIG. 9 are explanatory illustrations of the configuration of the power transmission mechanism. FIG. 7 is an enlarged explanatory illustration showing surroundings of the pulley 170 and the rail portion 120. FIG. 8 is an illustration seen along an arrow A in FIG. 7. FIG. 9 is an enlarged perspective illustration showing surroundings of the pulley 170 and the rail portion 120.

The pulley 170 rotated by the driving force of the motor 187 has the outer peripheral surface 171 that is formed by a part of the first virtual conical surface having the first cone axis coincided with an axis of the output shaft of the motor 187. That is, such an outer peripheral surface 171 is formed in a taper shape. The outer peripheral surface 171 of the pulley 170 is provided with the wire groove 173 spirally circulating around the outer peripheral surface 171. The grip force sensation feedback device 100 is gripped by the user when used, thus a length of the pulley 170 in an axial direction is set to, for example, 8 to 15 mm and a diameter of a large diameter portion may be set to, for example, Φ5 to Φ8 mm. This can prevent an increase in size of the grip force sensation feedback device 100.

The rail portion 120 includes the opposed surface 128 that is opposed to the outer peripheral surface of the pulley 170. Such an opposed surface 128 is formed by a part of the second virtual conical surface having the axis of the rotating shaft member 151 as the second cone axis. A first guide portion 121 and a second guide portion 123 for guiding the wire 135 are provided on the opposed surface 128 of the rail portion 120 along a circumferential direction of the second virtual conical surface. The first guide portion 121 and the second guide portion 123 are each formed, for example, as a wall portion with a predetermined length protruding from the opposed surface 128.

Figure 10:
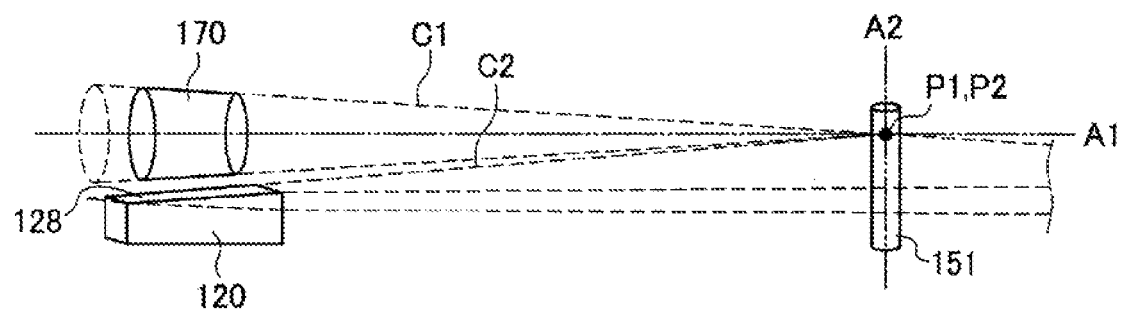
FIG. 10 is an explanatory illustration of an outer peripheral surface of a pulley and an opposed surface of a rail portion.

FIG. 10 is an explanatory illustration showing a relationship between the outer peripheral surface 171 of the pulley 170 and the opposed surface 128 of the rail portion 120. The outer peripheral surface 171 of the pulley 170 is formed by a part of the first virtual conical surface C1 having the first cone axis A1. Further, the opposed surface 128 of the rail portion 120 is formed by a part of the second virtual conical surface C2 having the second cone axis A2. The first cone axis A1 is coincided with the axis of the output shaft of the motor 187 and a vertex P1 of the first virtual conical surface C1 is positioned at an intersection of the first cone axis A1 and the axis of the rotating shaft member 151. Further the second cone axis A2 is coincided with the axis of the rotating shaft member 151 and perpendicular to the first cone axis A1. A vertex P2 of the second virtual conical surface C2 is positioned on the second cone axis A2 and substantially coincided with the vertex P1 of the first virtual conical surface C1.

A diameter of the second virtual conical surface C2 in a part forming the opposed surface 128 of the rail portion 120 is made larger than a diameter of the first virtual conical surface C1 in a part forming the outer peripheral surface 171 of the pulley 170. Thus, a rotation speed of the pulley 170 driven by the motor 187 is transmitted to the rail portion 120 with a reduction in speed. This allows the smooth operation by the motor 187 even if a rotation torque to be transmitted to the rail portion 120 is small.

In the grip force sensation feedback device 100 according to the present embodiment, a radius of a bottom surface of the second virtual conical surface C2, that is, a distance from the rotating shaft member 151 to a front end portion of the rail portion 120 can be set to a value close to a distance from the joint at the root of the forefinger to the tip of the forefinger. This allows the link 110 to rotate around the rotating shaft member 151 correspondingly to the movement of the forefinger, thereby facilitating the operation of the grip force sensation feedback device 100 by the user.

Back to FIG. 7 to FIG. 9, the wire 135 as a means for transmitting the rotation torque of the pulley 170 to the rail portion 120 is wound around the pulley 170. The wire 135 is wound along the wire groove 173 in a spiral shape formed on the outer peripheral surface 171 of the pulley 170. Between both end portions of the wire 135 wound around the pulley 170, the wire 135 led out from a front side end portion having a larger diameter is guided by the first guide portion 121 to be arranged. Further, between the both end portions of the wire 135 wound around the pulley 170, the wire 135 led out from a rear side end portion having a smaller diameter is guided by the second guide portion 123 to be arranged.

The end portion of the wire 135 arranged along the first guide portion 121 is led to a rear side of the opposed surface 128 via a hole 125 formed in the rail portion 120 and fixed by a fixing means such as a screw. Further, between the both end portions of the wire 135, the end portion of the wire 135 arranged along the second guide portion 123 is led to the rear side of the opposed surface 128 via a hole 127 formed in the rail portion 120 and fixed to one end of a spring 130 fixed to the rear side of the rail portion 120. In this configuration, the wire 135 is applied with a tension by virtue of an elastic force of the spring 130 to prevent loosening of the wire 135 on the pulley 170 and the rail portion 120. In the present embodiment, the spring 130 corresponds to a tension generating portion that applies a tension to the wire 135.

In this configuration, the wire 135 is wound around the pulley 170 and the rail portion 120 on their surfaces, each of which is formed by a part of the corresponding conical shape. The opposed surface 128 of the rail portion 120 is formed by a part of the conical surface projecting toward the pulley 170. This configuration, along with the tension of the wire 135, can prevent the wire 135 arranged along the first guide portion 121 and the second guide portion 123 on the rail portion 120 from becoming loose from the opposed surface 128.

However, since the opposed surface of the rail portion 120 is formed by a part of the conical surface, the tension of the wire 135 may cause the wire 135 to slide over the opposed surface 128 of the rail portion 120 and the wire 135 may be displaced from a sending-out position to the pulley 170 or a winding position from the pulley 170. Thus, the first guide portion 121 and the second guide portion 123 are arranged an the opposed surface 128 of the rail portion 120 and the wire 135 on the rail portion 120 is pressed against the first guide portion 121 and the second guide portion 123 by the tension. This prevents the displacement of the wire 135. In this configuration, the wire 135 arranged along the first guide portion 121 and the second guide portion 123 is positioned at the winding position of the pulley 170 or the sending-out position from the pulley 170 regardless of the rotation angle of the pulley 170 and the position of the rail portion 120. Thus, the wire 135 is appropriately arranged along the wire groove 173 when being wound around the pulley 170, thereby allowing the smooth operation of the power transmission mechanism.

A depth of the wire groove 173 arranged on the outer peripheral surface 171 of the pulley 170 may be set to be, for example, equal to or less than a radius of the wire 135. Further, a height (a protrusion width) of the first guide portion 121 and the second guide portion 123 arranged on the opposed surface 128 of the rail portion 120 may be set to be equal to or more than the radius of the wire 135 and equal to or less than a diameter of the wire 135. In the case where the depth of the wire groove 173 and the height of the first guide portion 121 and the second guide portion 123 are set to such ranges, it becomes possible to prevent the displacement of the wire 135 on the pulley 170 and the rail portion 120 and also significantly reduce a gap and rattling of the wire 135 occurring when the wire 135 is wound around the pulley 170 or sent out to the rail portion 120 by putting the pulley 170 and the rail portion 120 close to each other.

Figure 11:
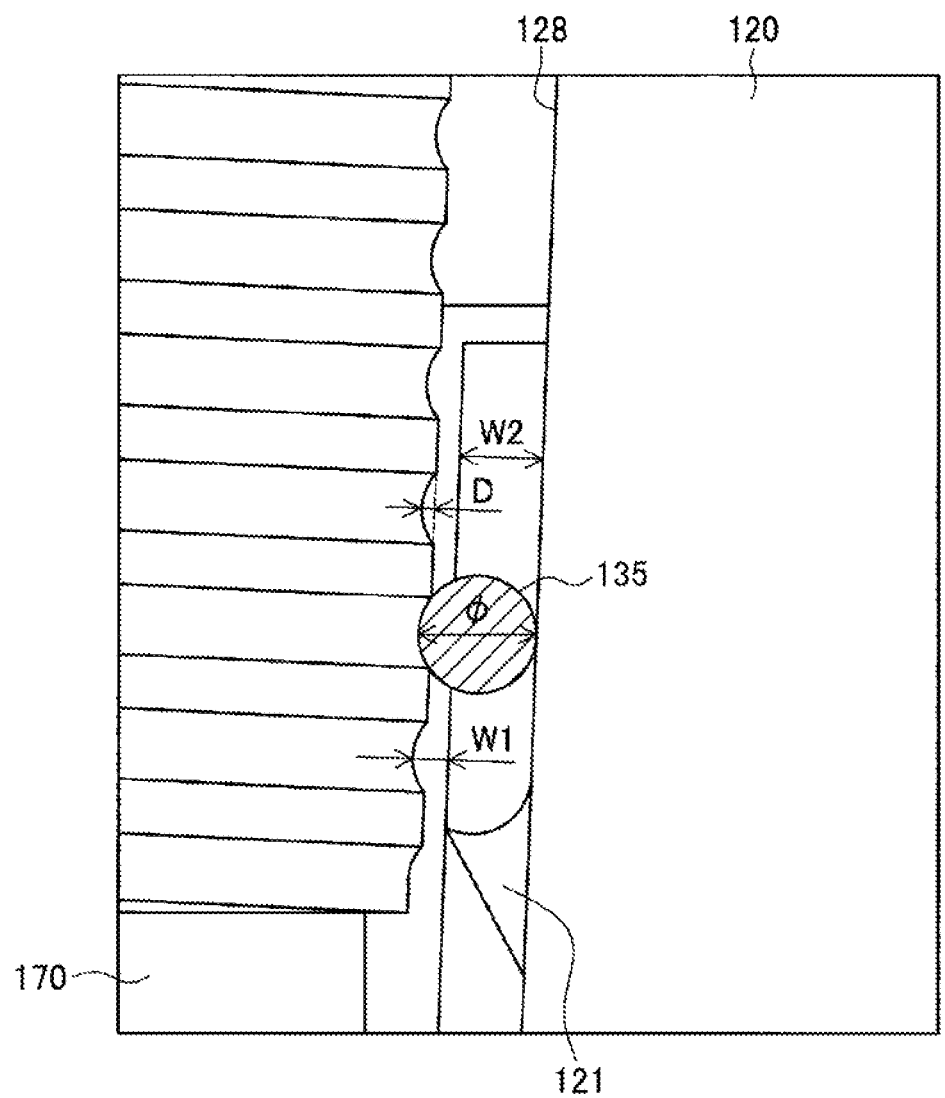
FIG. 11 is an explanatory illustration of a configuration of the power transmission portion.

FIG. 11 is an illustration that explains the depth D of the wire groove 173, the height W2 of the first guide portion 121 and the second guide portion 123, and the distance W1 between the pulley 170 and the rail portion 120. The depth D of the wire groove 173 formed on the pulley 170 is equal to or less than the radius ($\Phi/2$) of the ire 135 and the width W2 of the first guide portion 121 is equal to or more than the radius ($\Phi/2$) of the wire 135 and equal to or less than the diameter ($\Phi$) of the wire 135. Further, the distance W1 between a bottom portion of the wire groove 173 and the first guide portion 121 is equal to or less than the diameter $\Phi$ of the wire 135. As described above, the both end portions of the wire 135 are fixed to the rear side of the opposed surface 128 to apply a tension to the wire 135. Thus, the wire 135 is pressed against the first guide portion 121 while being held by the wire groove 173 positioned such that the wire groove 173 is opposed to the first guide portion 121. This configuration reduces a gap and rattling of the wire 135 not to cause the displacement of the wire 135.

Further, as shown in FIG. 11, the wire groove 173 of the pulley 170 is formed in an arc shape, thus the wire 135 wound around the wire groove 173 with a predetermined tension is hardly displaced. Similarly, the surface of the rail portion 120 in the first guide portion 121 and second guide portion 123, where the wire 135 is arranged, is formed in an arc shape, thus the wire 135 arranged on the surface of the rail portion 120 with a predetermined tension is hardly displaced.

Further, as described above, the position of the link 110 can be adjusted along the axial direction of the rotating shaft member 151 by loosening the fixing screw 159 arranged in a rear end portion of the link 110, moving a position of the link 110 to an appropriate position, and then tightening the fixing screw 159 again. This makes it possible to adjust the distance W1 between the opposed surface 128 of the rail portion 120 and the outer peripheral surface 171 of the pulley 170. In this manner, an appropriate preload can be applied to the wire 135 to prevent the displacement of the wire 135.

Further, the first guide portion 121 and the second guide portion 123 are each formed in an arc shape in a plan view. Curvature radiuses of the first guide portion 121 and the second guide portion 123 gradually change along arrangement directions of the first guide portion 121 and the second guide portion 123. As an example, this will be explained by referring to FIG. 7. A distance from a site where the wire 135 is sent out the pulley 170 to the first guide portion 121 to the second cone axis A2 and a distance from a site where the wire 135 is wound around the pulley 170 from the first guide portion 121 to the second cone axis A2 change depending on the rotation of the pulley 170 or the rail portion 120. Thus, even if the rotation angles of the pulley 170 are the same, a length of the wire 135 being wound around the pulley 170 from the rail portal 120 or a length of the wire 135 being sent out from the pulley 170 to the rail portion may vary.

In the grip force sensation feedback device 100 according to the present embodiment, the outer peripheral surface 171 of the pulley 170 and the opposed surface 128 of the rail portion 120 are both conically shaped and angles of their conical surfaces are appropriately adjusted. Thus, an amount of the wire 135 being sent out from the pulley 170 to the first guide portion 121 or the second guide portion 123 and an amount of the wire 135 being wound around the first guide portion 121 or the second guide portion 123 are made coincident with each other. Similarly, an amount of the wire 135 being sent out from the first guide portion 121 or the second guide portion 123 to the pulley 170 and an amount of the wire 135 being wound around the pulley 170 are made coincident with each other.

Figure 12:
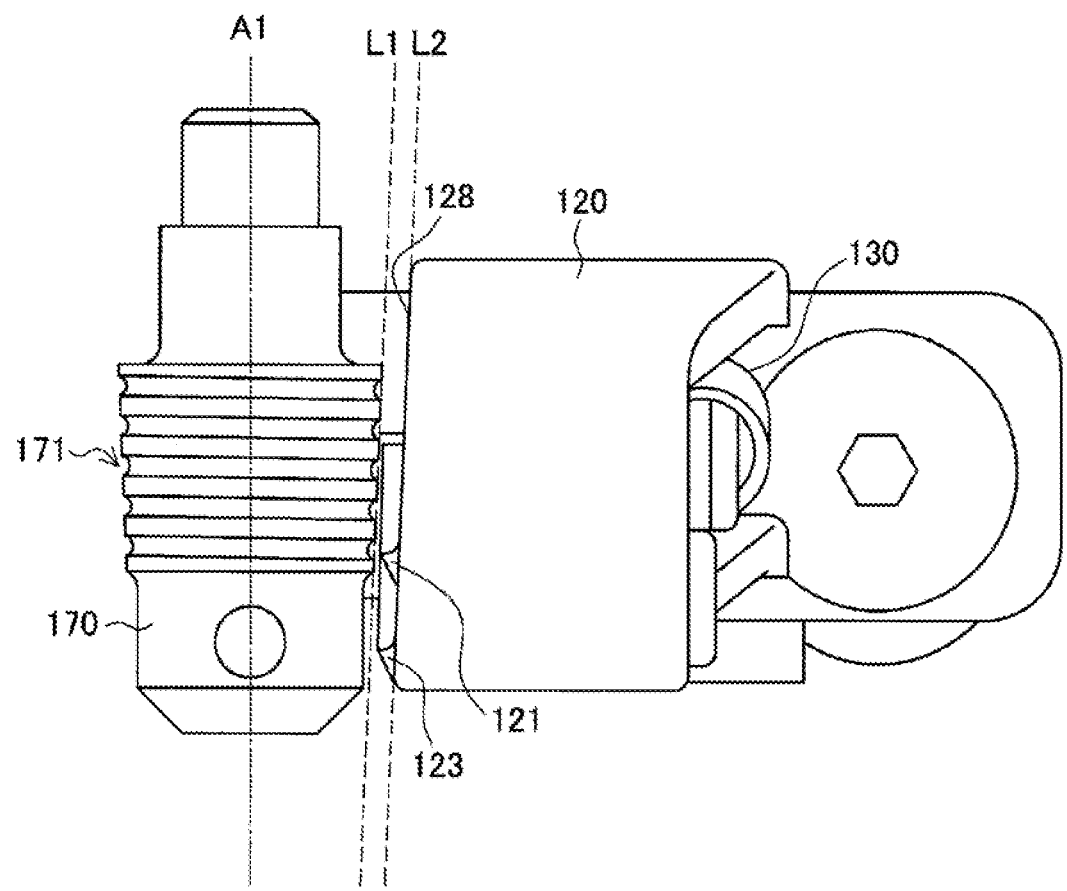
FIG. 12 is an explanatory illustration of a configuration of the power transmission portion.

FIG. 12 is an illustration that explains an inclination angle of the outer peripheral surface 171 of the pulley 170 and an inclination angle of the opposed surface 128 of the rail portion 120. FIG. 12 shows a ridge line L1 formed by the outer peripheral surface 171 of the pulley 170 and a ridge line L2 formed by the opposed surface 128 of the rail portion 120 at a position where the outer peripheral surface 171 of the pulley 170 and the opposed surface 128 of the rail portion 120 come closest to each other. As shown in FIG. 12, at the position where the outer peripheral surface 171 of the pulley 170 and the opposed surface 128 of the rail portion 120 come closest to each other, an angle formed by the ridge line L1 of the outer peripheral surface 171 the pulley 170 relative to the first cone axis (the axis of the pulley 170) A1 and an angle formed by the ridge line L2 of the opposed surface 128 of the rail portion 120 relative to the first cone axis A1 are coincided with each other. These angles are set so that the amount of the wire 135 being sent out from the pulley 170 to the rail portion 120 and the amount of the wire 135 being wound around the pulley 170 from the rail portion 120 are coincided with each other. Such a configuration can prevent loosening or tightening of the wire 135 caused by the rotation of the pulley 170 and the rail portion 120, thereby allowing smooth operation of the power transmission mechanism.

Further, a stopper 126 is provided in the rail portion 120. The stopper 126 has a function of preventing the wire 135 front being cut by impact when the rail portion 120 reaches a limit of a movable range. In this configuration, in a case where the rail portion 120 is pressed by the operation of the user, the stopper 126 is abutted to the casing 101 before the rail portion 120 reaches the limit of the movable range defined by an arrangement region of the wire 135 to restrict a rotation range of the rail portion 120. Further, in a case where the rail portion 120 is rotated in an opposite direction, a rear end portion of the link 110 supported by the rotating shaft member 151 is abutted to the bearing portion 155 to restrict the rotation range of the rail portion 120.

Figure 13:
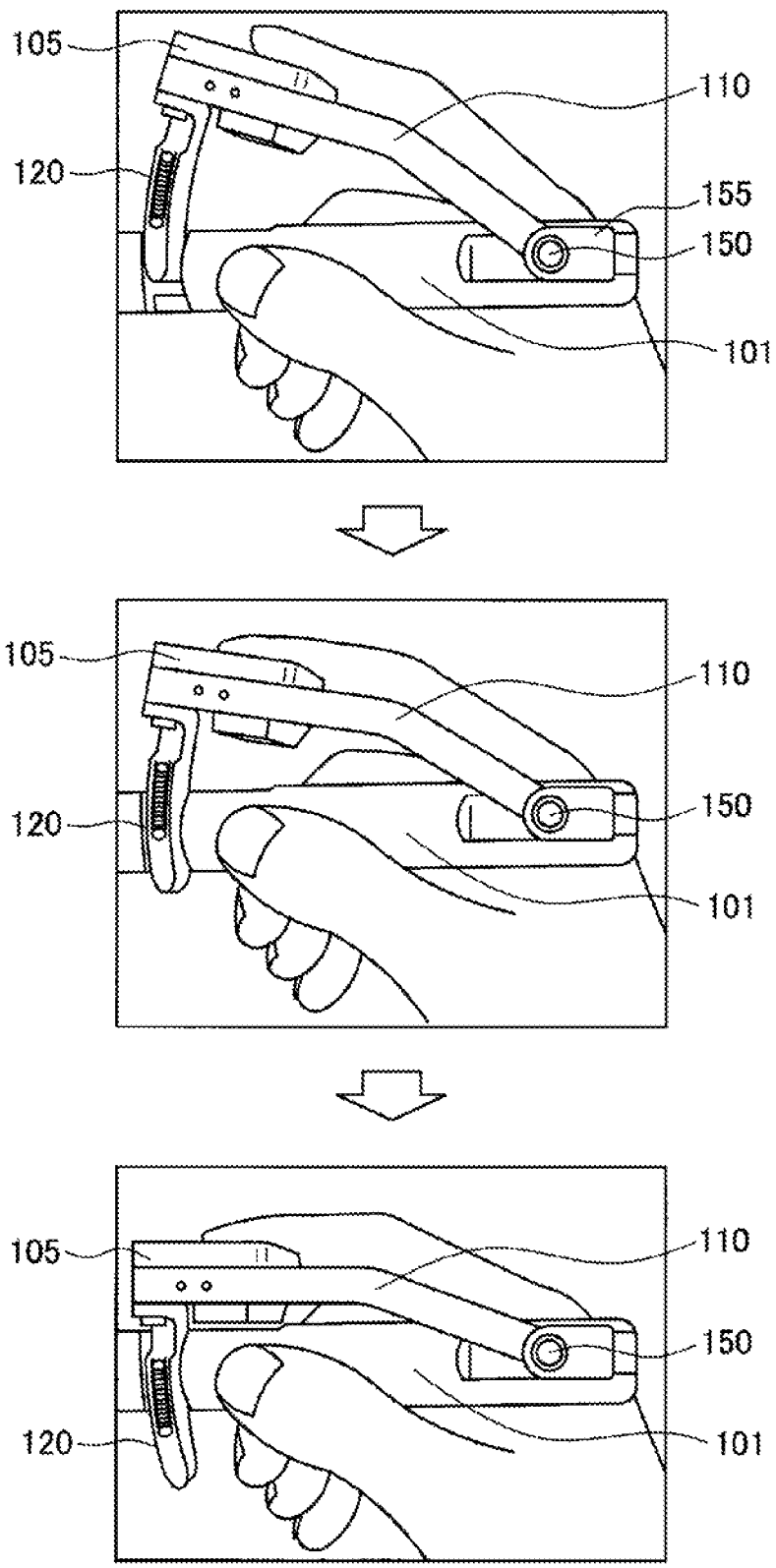
FIG. 13 is an explanatory illustration showing how the grip force sensation feedback device is used.
Figure 14:
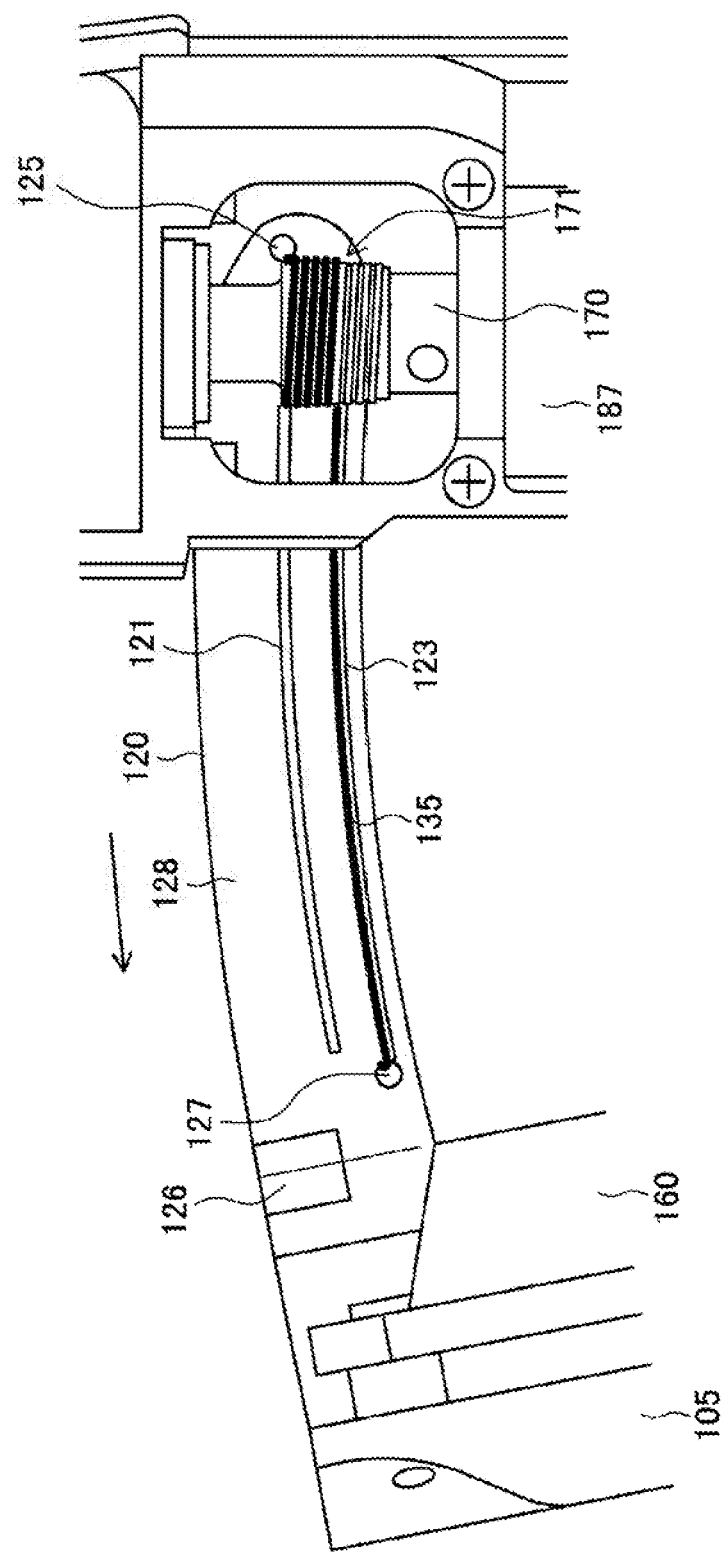
FIG. 14 is an explanatory illustration showing an operation of the power transmission portion.
Figure 15:
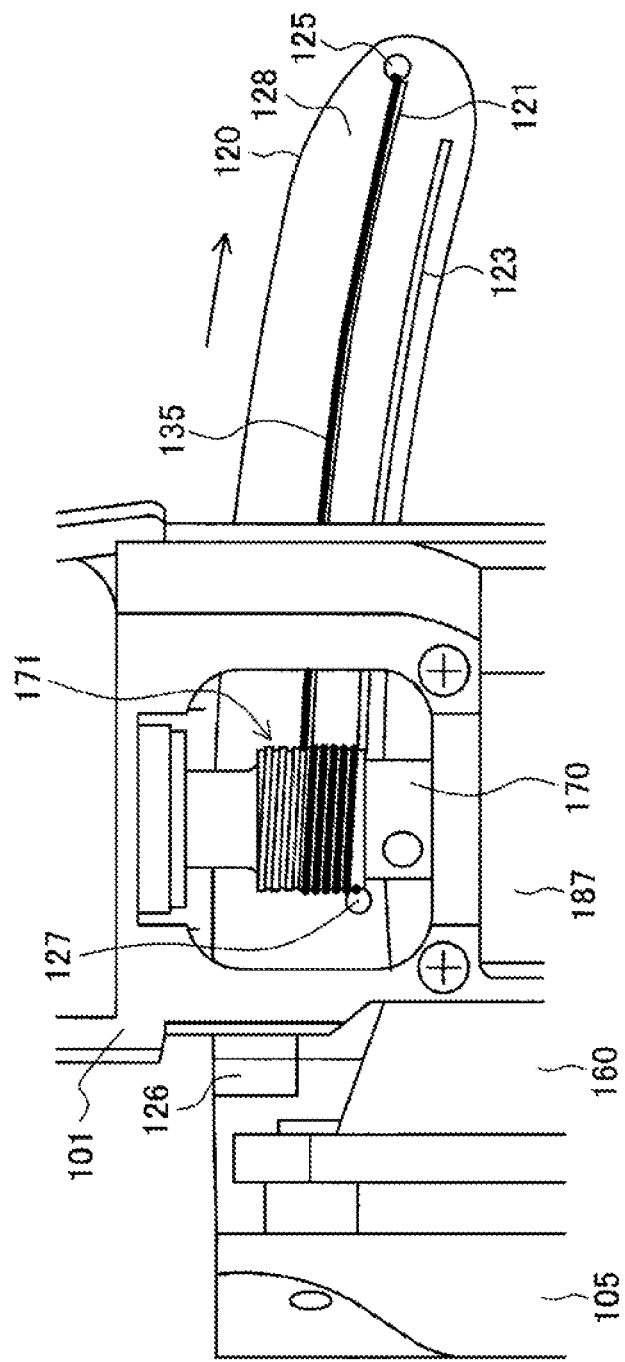
FIG. 15 is an explanatory illustration showing an operation of the power transmission portion.

FIG. 13 shows how the link 110 and the rail portion 120 are rotated by the user. An upper panel of FIG. 13 shows a state in which the link 110 and the rail portion 120 are positioned at their origin positions. The pulley 170 is opposed to the opposed surface 128 at a tip side of the rail portion 120 (see FIG. 14). In this state, the rear end of the link 110 is abutted to the bearing portion 155 to restrict the maximum movable region of the line 110 and the rail portion 120. Further, a middle panel of FIG. 13 shows a state in which the link 110 and the rail portion 120 are pressed to approximately a half of the movable region. The pulley 170 is opposed to the opposed surface 128 at a central portion of the rail portion 120 (see FIG. 7). Further, a lower panel of FIG. 13 shows a state in which the link 110 and the rail portion 120 are most pressed. The pulley 170 is opposed to the opposed surface 128 at a base side of the rail portion 120. In this state, the stopper 126 is abutted to the casing 101 to restrict the maximum movable region of the link 110 and the rail portion 120 (see FIG. 15). The wire 135 is prevented from being cut by restricting the maximum movable region of the link 110 and the rail portion 120 in this manner.

<4. Usage Example>

Hitherto the overall configuration of the grip force sensation feedback device 100 and the configuration of the power transmission mechanism have been described. Hereinafter, a usage example of the medical apparatus 10 including the grip force sensation feedback device 100 according to the present embodiment will be briefly described.

(4-1. Remote Operation of Grip-Type Surgical Instrument)

First, a remote operation of the grip-type surgical instrument as a basic usage of the medical apparatus 10 will be described. The user such as a surgeon grips the grip force sensation feedback device 100 to move it to a desired position and change its direction to an appropriate direction. The control portion of the medical apparatus 10 detects information regarding the axial rotation angles and the angles of the joints of the supporting arm portion 20 that supports the grip force sensation feedback device 100. In this operation, the control portion detects a moment of the translational operation or torsion operation applied to the grip force sensation feedback device 100 on the basis of a sensor signal of the force sensor provided between the grip force sensation feedback device 100 and the fourth arm portion 20*d*. The control portion outputs a command for controlling the arm of the slave side robot apparatus on the basis of the detected attitude and moment of the supporting arm portion 20 to control a position and direction of the grip-type surgical instrument supported by the slave side robot apparatus.

Further, when the user presses the finger contact portion 105 of the grip force sensation feedback device 100 by his/her forefinger the like, the link 110 is rotated around the rotating shaft member 151. When the rail portion 120 is rotated with the rotation of the link 110, the pulley 170 is rotated via the wire 135, thereby inputting the rotation torque to the motor 187. A rotation speed and a rotation angle of such a motor 187 are detected by the encoder 185. Then, the control portion outputs a command for controlling the grip-type surgical instrument supported by the slave side robot apparatus on the basis of the information detected by the encoder 185 to control the gripping operation of the grip-type surgical instrument.

Figure 16:
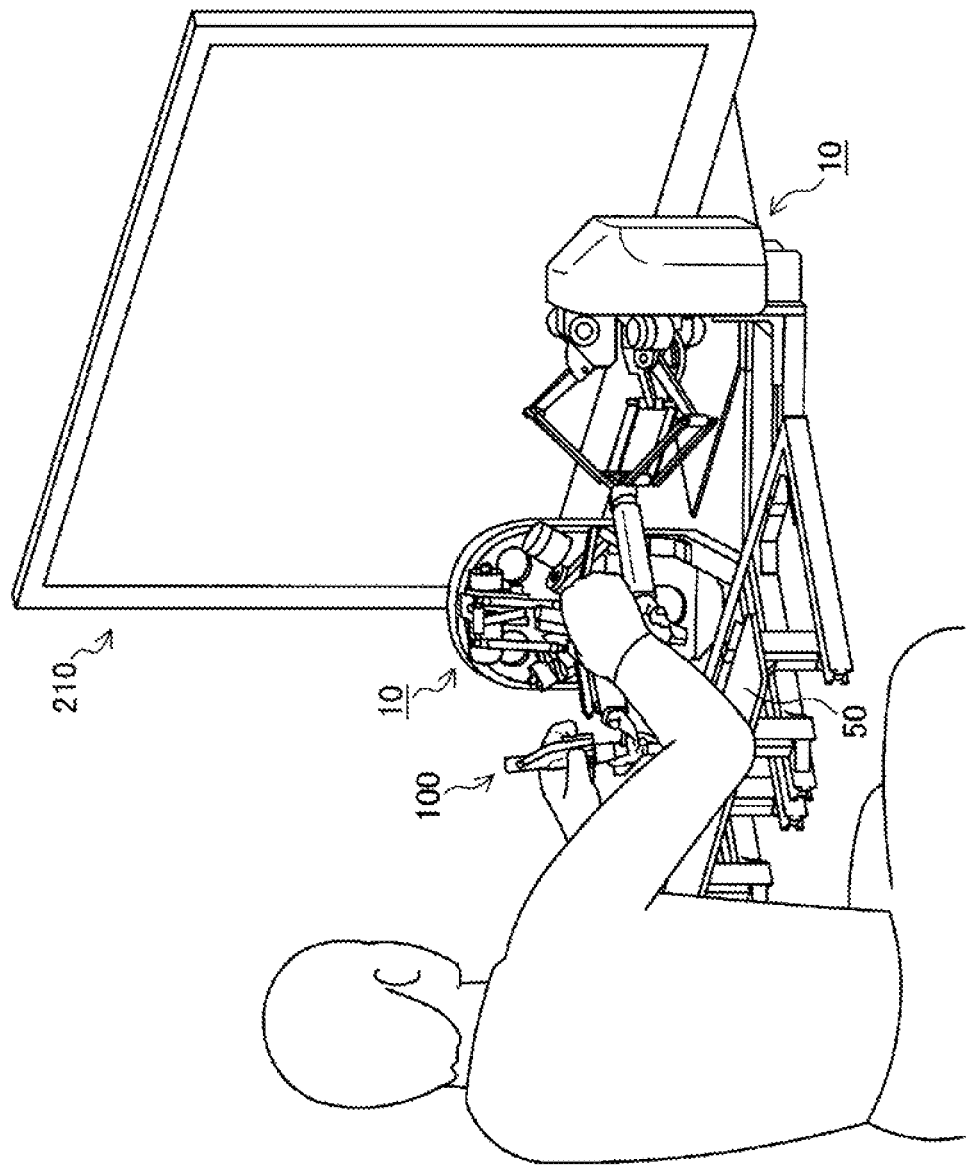
FIG. 16 is an explanatory illustration showing a use example of the medical apparatus according to the embodiment.

FIG. 16 shows an example of using the medical apparatus 10 according to the present embodiment. In FIG. 16, two medical apparatuses 10 are arranged side by side and the user grips the respective grip force sensation feedback devices 100 by the right hand and the left hand while placing both arms or elbows on the supporting stands 50. In this state, the user operates the medical apparatus 10 while viewing a monitor 210 that displays an operation field. The user operates two medical apparatuses 10 to change positions or directions of the respective grip-type surgical instruments held by the slave side robot apparatuses not illustrated or perform the gripping operation of the respective grip-type surgical instruments.

(4-2. Force Sensation Feedback)

Next, a force sensation feedback operation of the medical apparatus 10 will be described. The slave side robot apparatus not illustrated includes a sensor for detecting a reaction force or external force applied to the arm that supports the grip-type surgical instrument. Such a sensor may be, for example, an encoder provided in a joint portion of the arm. In this case, the encoder can detect a torque applied to a motor provided in the joint portion. The control portion acquires information regarding the torque applied to the joint portion of the slave side robot apparatus and controls a driving torque of the motor 35 that controls the supporting arm portion 20 of the medical apparatus 10. In this manner, the user operating the grip force sensation feedback device 100 can be provided with a force sensation feedback corresponding to the external force applied to the grip-type surgical instrument supported by the slave side robot apparatus.

Further, the slave side robot apparatus not illustrated includes a sensor for detecting a reaction force received from the gripping operation of the grip-type surgical instrument. Such a sensor may be, for example, an encoder connected to a motor that operates the grip-type surgical instrument. In this case, the encoder can detect a torque applied to the motor. The control portion acquires information regarding the reaction force received from the gripping operation of the grip-type surgical instrument and controls a driving torque of the motor 187 provided in the grip force sensation feedback device 100. During this operation, a driving torque is generated in a direction opposite to the rotation direction of the pulley 170 that is caused when the user presses the finger contact portion 105 of the grip force sensation feedback device 100 by his/her forefinger. In this manner, the reaction force generated when an object matter is gripped by the grip-type surgical instrument of the slave side robot apparatus is provided to the user as a feedback to allow the user to sense the force sensation.

(4-3. Origin Returning Operation)

Next, an origin returning operation of the grip force sensation feedback device 100 will be described. When the user completes the pressing operation of the finger contact portion 105 by his/her forefinger or the like, the torque inputted from the pulley 170 to the motor 187 becomes zero. In this case, the control portion stops the control of the grip-type surgical instrument of the slave side robot apparatus not to perform the gripping operation of the grip-type surgical instrument and returns the power transmission mechanism of the grip force sensation feedback device 100 to an origin position. As described above, the grip force sensation feedback device 100 includes the origin sensor for setting the origin position of the link 110 and the control portion drives the motor 187 until the link 110 is returned to the origin position. In this configuration, when the user does not perform the gripping operation, the power transmission mechanism can be returned to the origin position and the grip-type surgical instrument is returned to an opened condition.

Note that, when the gripping operation is not performed by the grip force sensation feedback device 100, the power transmission mechanism may be returned to the origin position without using the origin returning operation control described above. For example, the link 110 may be mechanically returned to the origin position using a member imparting an elastic force, such as a spring. Alternatively, the link 110 may be returned to the origin position by arranging a finger fixing portion in the finger contact portion 105 and fixing the forefinger or the like to the finger contact portion 105.

<5. Summary>

As described above, the grip force sensation feedback device 100 according to the present embodiment transmits the rotation torque between the pulley 170 and the rail portion 120, each of which is formed by a part of the corresponding virtual conical surface, using the wire 135 as a power transmission means. The grip force sensation feedback device 100, which includes in its inside the motor 187, the encoder 185, and the origin sensor, is constituted as a stylus-structure device having a pen shape to be easily gripped by the user, thus the device is made compact.

Further, in the grip force sensation feedback device 100 according to the present embodiment, for example, the diameter of the large diameter portion of the pulley 170 may be set to Φ5 to Φ8 mm and the diameter of the conical surface including the opposed surface 128 of the rail portion 120 may be set to Φ150 to Φ200 mm. Thus, the device is made compact despite having the large reduction ratio for transmitting the rotation torque from the pulley 170 to the rail portion 120. Further, the grip force sensation feedback device 100 can provide the force sensation feedback to the gripping force regardless of the width of the object matter to be gripped.

Further the grip force sensation feedback device 100 according to the present embodiment uses the wire 135 as the power transmission means and is thus made light in weight. Further, the grip force sensation feedback device 100 transmits the power between the pulley 170 and the rail portion 120 using the wire 135 as the power transmission means. This configuration can reduce a resistance during the winding operation as compared to a case of using a belt as the power transmission means. Further, the grip force sensation feedback device 100, which transmits the power between the pulley 170 and the rail portion 120 using the wire 135 as the power transmission means, does not include a gear structure, thus backlash is prevented. As a result, the grip force sensation feedback device 100 can prevent the generation of noise even when transmitting a feeble force.

Further, the grip force sensation feedback device 100, which transmits the power between the pulley 170 and the rail portion 120 using the wire 135 as the power transmission means, can smoothly switch the rotation directions of the pulley 170 and the rail portion 120. Thus, the encoder 185 can detect a change in the rotation angle of the motor 187 caused by the external force, thereby allowing the easy execution of a bilateral control.

Further, in the rail portion 120, the first guide portion 121 and the second guide portion 123 are arranged so as to correspond to the position where the wire 135 is wound around the pulley 170 and the position where the wire 135 is sent out from the pulley 170 regardless of the rotation angles of the pulley 170 and the rail portion 120. Thus, the power transmission mechanism can operate smoothly without having a gap and rattling or twisting of the wire 135.

Further, in the grip force sensation feedback device 100 according to the present embodiment, the inclination angle of the outer peripheral surface 171 of the pulley 170 and the inclination angle of the opposed surface 128 of the rail portion 120 are set so that the amount of the wire 135 being sent out from the pulley 170 to the rail portion 120 and the amount of the wire 135 being wound around the pulley 170 from the rail portion 120 are coincided with each other. Thus, the power transmission mechanism can operate smoothly without having loosening or tightening of the wire 135.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the above embodiment, the grip force sensation feedback device is formed in a writing pen shape, however, the present technology is not limited to such an example. For example, the grip force sensation feedback device may be formed in a scissors shape. For example, the rotation shaft of the link where the rail portion is provided may be arranged on a front side and the link and the rail portion may be rotated when the user grips the device.

Further, the power transmission mechanism including the pulley, the rail portion, and the wire, described in the above embodiment, may be applied to an appropriate device requiring a smooth and light force transmission or the like, other than the grip force sensation feedback device.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A grip force sensation feedback device including:
a first rotary member that has an outer peripheral surface including a part of a first virtual conical surface, the first rotary member being rotated around a first cone axis;
a second rotary member that has an opposed surface which includes a part of a second virtual conical surface and which is opposed to the outer peripheral surface of the first rotary member, the second rotary member being rotated around a second cone axis;
a wire that has both end portions connected to the second rotary member and that has a central portion wound around the first rotary member; and
a driving portion that provides a force sensation feedback to a finger of a user in contact with the second rotary member by rotating the first rotary member and thereby causing a rotation of the second rotary member.

(2)
The grip force sensation feedback device according to (1), in which the first cone axis and the second cone axis are orthogonal to each other.

(3)
The grip force sensation feedback device according to (1) or (2), in which one end of the wire wound around the first rotary member is sent out to the second rotary member and the other end of the wire is wound around from the second rotary member by the rotation of the first rotary member or the second rotary member.

(4)
The grip force sensation feedback device according to any one of (1) to (3), in which the first rotary member includes a wire groove spirally circulating around the outer peripheral surface.

(5)
The grip force sensation feedback device according to any one of (1) to (4), in which the second rotary member includes a guide portion that defines an arrangement position of the wire on the opposed surface.

(6)
The grip force sensation feedback device according to (5), in which a distance between the guide portion of the second rotary member and the outer peripheral surface of the first rotary member is smaller than a diameter of the wire.

(7)
The grip force sensation feedback device according to (5) or (6), in which the guide portion includes a first guide portion and a second guide portion, each of which is arranged along a circumferential direction of the second virtual conical surface.

(8)
The grip force sensation feedback device according to (7), in which the first guide portion defines an arrangement position of the wire extending from the one end of the wire wound around the first rotary member, and the second guide portion defines an arrangement position of the wire extending from the other end of the wire wound around the first rotary member.

(9)
The grip force sensation feedback device according to (7) or (8), in which the first guide portion and the second guide portion are an arc shapes in a plan view, and curvature radiuses of the first guide portion and the second guide portion gradually change along arrangement directions of the first guide portion and the second guide portion.

(10)

The grip force sensation feedback device according to any one of (7) to (9), in which the first guide portion is an arc shape in a plan view, and even in a case where a position of the second rotary member is changed by the rotation of the second rotary member, a position of the first guide portion is coincided with a lead-out position of the one end of the wire wound around the first rotary member.

(11)

The grip fore sensation feedback device according to any one of (7) to (10), in which the second guide portion is an arc shape in a plan view, and even in a case where a position of the second rotary member is changed by the rotation of the second rotary member, a position of the second guide portion is coincided with a lead-out position of the other end of the wire wound around the first rotary member.

(12)

The grip force sensation feedback device according to any one of (1) to (11), in which the second rotary member includes a finger contact portion that is pressed by the finger of the user.

(13)

The grip force sensation feedback device according to any one of (1) to (12), including
an adjusting portion that adjusts a distance between the outer peripheral surface of the first rotary member and the opposed surface of the second rotary member.

(14)

The grip force sensation feedback device according to any one of (1) to (13), including
a tension generating portion that applies a tension to the wire.

(15)

The grip force sensation feedback device according to any one of (1) to (14), including
an origin sensor that defines a reference position of the second rotary member.

(16)

The grip force sensation feedback device according to any one of (1) to (15), in which the grip force sensation feedback device is an input device that performs a remote operation of a medical surgical instrument.

(17)

The grip force sensation feedback device according to (16), in which the medical surgical instrument is forceps, tweezers, or a cutting implement.

(18)

A stylus-type force sensation feedback device including:
a rotary member that rotates with a gripping operation performed by a user; and
a driving portion that provides a force sensation feedback to the user by applying a rotation torque to the rotary member in a direction opposite to a rotation direction caused by the gripping operation performed by the user.

REFERENCE SIGNS LIST

100 grip force sensation feedback device (stylus-type force sensation feedback device)
105 finger contact portion
110 link
120 rail portion (second rotary member)
121 first guide portion
123 second guide portion
135 wire
170 pulley (first rotary member)
185 encoder
187 motor

The invention claimed is:

1. A grip force sensation feedback device comprising:
a first rotary member that has an outer peripheral surface including a part of a first virtual conical surface, the first rotary member being rotated around a first cone axis;
a second rotary member that has an opposed surface and rotates around a second cone axis, wherein the opposed surface is formed by a part of a second virtual conical surface and is opposed to the outer peripheral surface of the first rotary member;
a wire that has both end portions connected to the second rotary member and that has a central portion wound around the first rotary member; and
a motor that provides a force sensation feedback to a finger of a user in contact with the second rotary member by rotating the first rotary member and thereby causing a rotation of the second rotary member.

2. The grip force sensation feedback device according to claim 1, wherein the first cone axis and the second cone axis are orthogonal to each other.

3. The grip force sensation feedback device according to claim 1, wherein rotation of the first rotary member or the second rotary member causes one end of the wire wound around the first rotary member to be sent out to the second rotary member, and another end of the wire to be wound around from the second rotary member.

4. The grip force sensation feedback device according to claim 1, wherein the first rotary member includes a spiral wire groove around the outer peripheral surface.

5. The grip force sensation feedback device according to claim 1, wherein the second rotary member includes a guide portion that defines an arrangement position of the wire on the opposed surface.

6. The grip force sensation feedback device according to claim 5, wherein a distance between the guide portion of the second rotary member and the outer peripheral surface of the first rotary member is smaller than a diameter of the wire.

7. The grip force sensation feedback device according to claim 5, wherein the guide portion includes a first guide portion and a second guide portion, each of which is arranged along a circumferential direction of the second virtual conical surface.

8. The grip force sensation feedback device according to claim 7, wherein the first guide portion defines an arrangement position of the wire extending from one end of the wire wound around the first rotary member, and the second guide portion defines an arrangement position of the wire extending from another end of the wire wound around the first rotary member.

9. The grip force sensation feedback device according to claim 8, wherein the first guide portion has an arc shape in a plan view, and even in a case where a position of the second rotary member is changed by the rotation of the second rotary member, a position of the first guide portion is coincided with a lead-out position of the one end of the wire wound around the first rotary member.

10. The grip force sensation feedback device according to claim 8, wherein the second guide portion has an arc shape in a plan view, and even in a case where a position of the second rotary member is changed by the rotation of the second rotary member, a position of the second guide portion is coincided with a lead-out position of the other end of the wire wound around the first rotary member.

11. The grip force sensation feedback device according to claim 7, wherein each of the first guide portion and the second guide portion have an arc shape in a plan view, and curvature radiuses of the first guide portion and the second guide portion gradually change along arrangement directions of the first guide portion and the second guide portion.

12. The grip force sensation feedback device according to claim 1, wherein the second rotary member includes a finger contact portion that is pressed by the finger of the user.

13. The grip force sensation feedback device according to claim 1, comprising
   an adjusting portion that adjusts a distance between the outer peripheral surface of the first rotary member and the opposed surface of the second rotary member.

14. The grip force sensation feedback device according to claim 1, comprising
   a spring member that applies a tension to the wire.

15. The grip force sensation feedback device according to claim 1, comprising
   a sensor that defines a reference position of the second rotary member as in original position.

16. The grip force sensation feedback device according to claim 1, wherein the grip force sensation feedback device is an input device that performs a remote operation of a medical surgical instrument.

17. The grip force sensation feedback device according to claim 16, wherein the medical surgical instrument is forceps, tweezers, or a cutting implement.

* * * * *